(12) United States Patent
Gong

(10) Patent No.: US 7,214,791 B2
(45) Date of Patent: May 8, 2007

(54) METHOD FOR PREPARATION OF 2'-DEOXY-2', 2'-DIFLUORO-β-CYTIDINE OR PHARMACEUTICALLY ACCEPTABLE SALTS THEREOF BY USING 1,6-ANHYDRO-β-D-GLUCOSE AS RAW MATERIAL

(75) Inventor: Chen Gong, Shenzhen (CN)

(73) Assignee: Shenzhen Hande Technology Co., Ltd., Shenzhen (CN)

( * ) Notice: Subject to any disclaimer, the term of this patent is extended or adjusted under 35 U.S.C. 154(b) by 491 days.

(21) Appl. No.: 10/883,462

(22) Filed: Jul. 1, 2004

(65) Prior Publication Data

US 2006/0003963 A1   Jan. 5, 2006

(51) Int. Cl.
*C07H 19/06*   (2006.01)
*A61K 31/7068*   (2006.01)

(52) U.S. Cl. .................. 536/28.3; 536/55.3; 514/49
(58) Field of Classification Search ................ 514/49; 536/28.3, 55.3
See application file for complete search history.

(56) References Cited

U.S. PATENT DOCUMENTS

| | | | |
|---|---|---|---|
| 4,965,374 A | 10/1990 | Chou et al. |
| 5,223,608 A | 6/1993 | Chou et al. |
| 5,252,756 A | 10/1993 | Chou et al. |
| 5,256,797 A | 10/1993 | Chou et al. |
| 5,256,798 A | 10/1993 | Chou et al. |
| 5,268,464 A | 12/1993 | Brill |
| 5,371,210 A | 12/1994 | Chou |
| 5,401,861 A | 3/1995 | Chou |
| 5,424,416 A | 6/1995 | Jones |
| 5,426,183 A | 6/1995 | Kjell |
| 5,430,026 A | 7/1995 | Hertel et al. |
| 5,434,254 A | 7/1995 | Chou et al. |
| 5,453,499 A | 9/1995 | Chou et al. |
| 5,480,992 A | 1/1996 | Hertel et al. |
| 5,521,294 A | 5/1996 | Wildfeuer |
| 5,541,345 A | 7/1996 | Hertel et al. |
| 5,559,222 A * | 9/1996 | Wirth ................ 536/28.5 |
| 5,594,124 A | 1/1997 | Chou |
| 5,594,155 A | 1/1997 | Hertel et al. |
| 5,606,048 A | 2/1997 | Chou et al. |
| 5,608,043 A | 3/1997 | Wirth |
| 5,633,366 A | 5/1997 | Takamatsu et al. |
| 5,633,367 A | 5/1997 | Kjell |
| 5,637,688 A | 6/1997 | Berglund |
| 5,648,473 A | 7/1997 | Chou |
| 5,744,597 A | 4/1998 | Chou et al. |
| 5,756,775 A | 5/1998 | Weigel |
| 5,808,047 A | 9/1998 | Kjell |
| 5,808,048 A | 9/1998 | Berglund |
| 5,821,357 A | 10/1998 | Chou et al. |
| 5,912,366 A | 6/1999 | Weigel |
| 5,945,547 A | 8/1999 | Chou et al. |
| 6,001,994 A | 12/1999 | Weigel |
| 6,680,382 B2 | 1/2004 | Bauta et al. |

FOREIGN PATENT DOCUMENTS

CN   1442420   9/2003

* cited by examiner

*Primary Examiner*—Shaojia Anna Jiang
*Assistant Examiner*—Ganapathy Krishnan
(74) *Attorney, Agent, or Firm*—Knobbe, Martens, Olson & Bear LLP

(57) ABSTRACT

The present invention provides a method for preparation of 2'-deoxy-2',2'-difluoro-β-cytidine or pharmaceutically acceptable salt thereof, comprising starting from 1,6-anhydro-β-D-glucose as raw material, oxidizing, and fluorinating to obtain 2-deoxy-2,2-difluoro-D-ribofuranose as intermediate. The 2'-deoxy-2',2'-difluoro-β-cytidine was finally prepared from the intermediate of 2-deoxy-2,2-difluoro-D-ribofuranose. The method is simple in operation and has a high yield. The method can effectively be used in large-scale production.

22 Claims, No Drawings

METHOD FOR PREPARATION OF 2'-DEOXY-2', 2'-DIFLUORO-β-CYTIDINE OR PHARMACEUTICALLY ACCEPTABLE SALTS THEREOF BY USING 1,6-ANHYDRO-β-D-GLUCOSE AS RAW MATERIAL

FIELD OF THE INVENTION

The present invention relates to the method for preparation of 2'-deoxy-2',2'-difluoro-β-cytidine or pharmaceutically acceptable salt thereof and its intermediate 2'-deoxy-2',2'-difluoro-D-ribofuranose.

BACKGROUND OF THE INVENTION

2'-deoxy-cytidine or its homologues as a medicine has good effect on treating viral diseases and cancer. At the moment, researches on this kind of compounds are attracting great interest in the art. Among these compounds, 2'-deoxy-2',2'-difluoro-β-cytidine hydrochloride (Gemcitabine hydrochloride), i.e. β-1-(2'-deoxy-2',2'-difluoro-D-ribofuranosyl)-4-aminopyrimidine-2-one hydrochloride is relatively well known, which has the following structure:

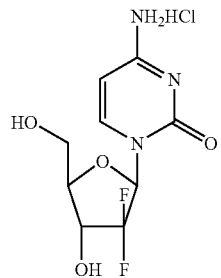

There are many methods for synthesizing β-1-(2'-deoxy-2',2'-difluoro-D-ribofuranosyl)-4-aminopyrimidine-2-one hydrochloride but it is mainly synthesized by the method using D-glyceraldehydes as the raw material and bromodifluoroacetate as the fluorinating agent. The method was described in detail in literature such as Hertel, L. W. et al., *J. Org. Chem.* 1988, 53:2406 and Chou, T. S. et al., *Synthesis* 1992, 565. β-1-(2'-deoxy-2',2'-difluoro-D-ribofuranosyl)-4-aminopyrimidine-2-one is a chiral compound. In the course of synthesis of using D-glyceraldehyde as the raw material, Reformasty reaction will be involved and the Reformasty reaction is a non-stereoselective reaction. In the preparation of the key intermediate 2-deoxy-2,2-difluoro-D-ribofuranose, it is not easy to control the stereoselective reaction. At the same time, in the course of synthesis, low boiling point anhydrous ether free from oxygen should be used as the reaction medium and the steps such as crystallization in solvent for resolution of isomers etc should be taken. As a result, both the yield and controllability of the reaction intermediate are low. Therefore the said method of synthesis seems to be not repeatable and not suitable for large-scale preparation.

SUMMARY OF THE INVENTION

The objective of the present invention is to provide a method for preparing 2'-deoxy-2',2'-difluoro-β-cytidine or pharmaceutically acceptable salt thereof and its intermediate 2'-deoxy-2',2'-difluoro-D-ribofuranose. In the present method, 1,6-anhydro-β-D-glucose i.e. laevo-glucose anhydride is used as the raw material. In the course of synthesis, stereoselective reaction can be fairly controlled and the chiral compound of 2'-deoxy-2',2'-difluoro-β-cytidine or pharmaceutically acceptable salt thereof and its key intermediate 2-deoxy-2,2-difluoro-D-ribofuranose can conveniently be obtained. The said method can be used in large-scale production effectively.

The present invention provides a method for preparing 2'-deoxy-2',2'-difluoro-β-cytidine or pharmaceutically acceptable salt thereof via 2-deoxy-2,2-difluoro-D-ribofuranose as intermediate, characterized in that starting from 1,6-anhydro-β-D-glucose as raw material, oxidizing, and fluorinating to obtain 2-deoxy-2,2-difluoro-D-ribofuranose as intermediate.

In particularly, the method of the present invention comprises:

(1) Oxidizing 1,6-anhydro-β-D-glucose to give 3-carbonyl-1,6-anhydro-β-D-glucose;
(2) Fluorinating and hydrolyzing 3-carbonyl-1,6-anhydro-β-D-glucose to give 3-deoxy-3,3-difluoro D-glucose;
(3) Condensing and dehydrating 3-deoxy-3,3-difluoro-D-glucose to give 2-deoxy-2,2-difluoro-ribofuranose; and
(4) Preparing 2'-deoxy-2',2'-difluoro-β-cytidine or pharmaceutically acceptable salt thereof from 2-deoxy-2,2-difluoro-D-ribofuranose.

In step (1) of the present invention, steps of protection and deprotection of hydroxyl groups of 1,6-anhydro-β-D glucose at position 2 and 4 are included. The said protective group for hydroxyl group is trimethylsilyl group. The protection of hydroxyl group is carried out in one or more anhydrous aprotic solvents selected from the group consisted of: dichloromethane, chloroform, carbon tetrachloride, 1,2-dichloroethane, 1,1-dichloroethane, 1,1,1-trichloroethane, 1,1,2-trichloroethane, ethyl acetate, propyl acetate, anisole, 1,2-methoxyethane, diethylene glycol ether, ethyl ether, n-butyl ether, isopropyl ether, dioxane, acetonitrile, tetrahydrofuran, nitromethane, nitroethane, and nitropropane. Among them, anhydrous dichloromethane or chloroform is preferred.

In the above-mentioned step for protection of hydroxyl group, diethylamine, triethylamine, n-propyl amine, di-isopropyl amine, n-butyl amine, isobutyl amine, 1,8-diazabicyclo(5.4.0.)undecene-7 (DBU), 2,6-dichlorobenzonitrile (DBN), N,N-dimethylphenylene urea (DMPU) or hexamethyl phosphamide (HMPA) are used as the acid-binding agent.

In the above-mentioned step for protection of hydroxyl group, 4,4-dimethylaminopyridine is used as the catalyst and the amount of the catalyst used is 0.01–5 mole %, preferably 0.1–1 mole % based on the amount of 1,6-anhydro-β-D-glucose. In the above-mentioned step for protection of hydroxyl group, the ratio in mole of 1,6-anhydro-β-D-glucose to trimethylchlorosilane is in a range of 1:2.0–3.2, preferably 1:2.0–2.2. Reaction temperature is in a range between −10° C. and 40° C., preferably between −5° C. and 25° C. Reaction time is in a range of 5 min −24 hr, preferably 10 min −10 hr.

In the oxidation reaction of the step (1) of the present invention, oxidant is selected from the group consisted of: PtO$_2$, Pt, CrO$_3$, Na$_2$CrO$_7$, PCC, PDC, KMnO$_4$, NaBrO$_3$, dimethyl sulfoxide (DMSC)/dicyclohexyl carbodiimide (DCC), DMSO/SOCl$_2$, DMSO/(CF$_3$COO)$_2$O, DMSO/TsCl (p-methyl benzene sulfochloride), ClO$_2$, or Dess-Martin reagent. Among them, 1,2-dichloropropylene (PDC), pyridinium chlorochromate (PCC) or Dess-Martin reagent (Chemical Name: 1,1,1-triacetoxy-1,1-dihydro-1,2-benziodoxol-3(1H)-one reagent) is preferable, Dess-Martin reagent is most preferable.

In step (2) of the present invention, the steps of protection and deprotection of hydroxyl groups at position 2 and 4 of 3-carbonyl-1,6-anhydro-β-D-glucose are included.

In step (2) of the present invention, the deprotection reaction is carried out in strong acid. The said strong acid is hydrochloric acid, sulfuric acid or trifluoroacetic acid.

In step (2) of the present invention, the fluorinating agent used in fluorination reaction is a complex of diethylamino sulfur trifluoride (DAST) and N,N-dimethylpropylene urea-hydrogen fluoride (DMPU-HF).

In step (3) of the present invention, the ortho-hydroxyl group of 3-deoxy-3,3-difluoro-D-glucose is oxidized by sodium periodate, condensed and dehydrated to obtain 2-deoxy-2 2-difluoro-D-ribofuranose.

In step (4) of the present invention, the steps of protection and deprotection of the hydroxyl groups of 2-deoxy-2,2-difluoro-D-ribofuranose are included. Preferably, the hydroxyl group at position 1 is protected first and then those at positions 3 and 5 are protected, wherein the protective group for protecting hydroxyl group at position 1 is mesyl group or acetyl group and those at positions 3 and 5 are benzoyl group or acetyl group.

In step (4) of the present invention, 2-deoxy-2,2-difluoro-D-ribofuranose is condensed with N'-cis-(2-cyanovinyl)-N,N-bis-trimethylsilyl urea, condensed and cyclized in methanol under the action of strong alkali, purified and salified to obtain 2'-deoxy-2',2'-difluoro-β-cytidine or pharmaceutically acceptable salt thereof.

In the present invention, the pharmaceutically acceptable salts of 2'-deoxy-2',2'-difluoro-β-cytidine are the salts that 2'-deoxy-2',2'-difluoro-β-cytidine is formed with any conventional inorganic acids or organic acids, provided that the said acid does not impair the pharmaceutical effect of 2'-deoxy-2',2'-difluoro-β-cytidine. The preferred salt is hydrochloride.

DETAILED DESCRIPTION OF THE PREFERRED EMBODIMENT

The each step of the method of the present invention will be described in detail as follows.

In the present invention, 1,6-anhydro-β-D-glucose i.e. laevo-glucose anhydride is used as the raw material and 2'-deoxy-2',2'-difluoro-β-cytidine or its pharmaceutically acceptable salts and its key intermediate 2'-deoxy-2',2'-difluoro-D-ribofuranose can be prepared effectively. 1,6-Anhydro-β-D-glucose is generally prepared from thermal degradation of starch. Detailed description of the method of preparation is given in literature such as: Zemplen, G. (Chem. Ber. 1931, 64:1545); Ward, R. B. (Methods Carbohydrate Chem. 1963, 2:394); Cerny, M. (Carbohydrate Chem. Biochem. 1977, 34:23). 1,6-Anhydro-β-D-glucose has relatively good crystallizing power. Its melting point is in the range of 182° C.–184° C. and its optical rotation is $[\alpha]^{18}$ is −66° C. (c=1, H$_2$O). It is relatively stable towards actions of many reagents due to its rigid stereo-structure. Therefore its use as the starting raw material will provide good controllability to the stereo-selective reaction in the course of synthesis. Key chiral intermediates of 2-deoxy-2,2-difluoro-D-ribofuranose and β-1-(2'-deoxy-2',2'-difluoro-D-ribofuranosyl)-4-aminopyrimidine-2-one hydrochloride can be obtained conveniently. The reaction Scheme provided by the present invention is as follows:

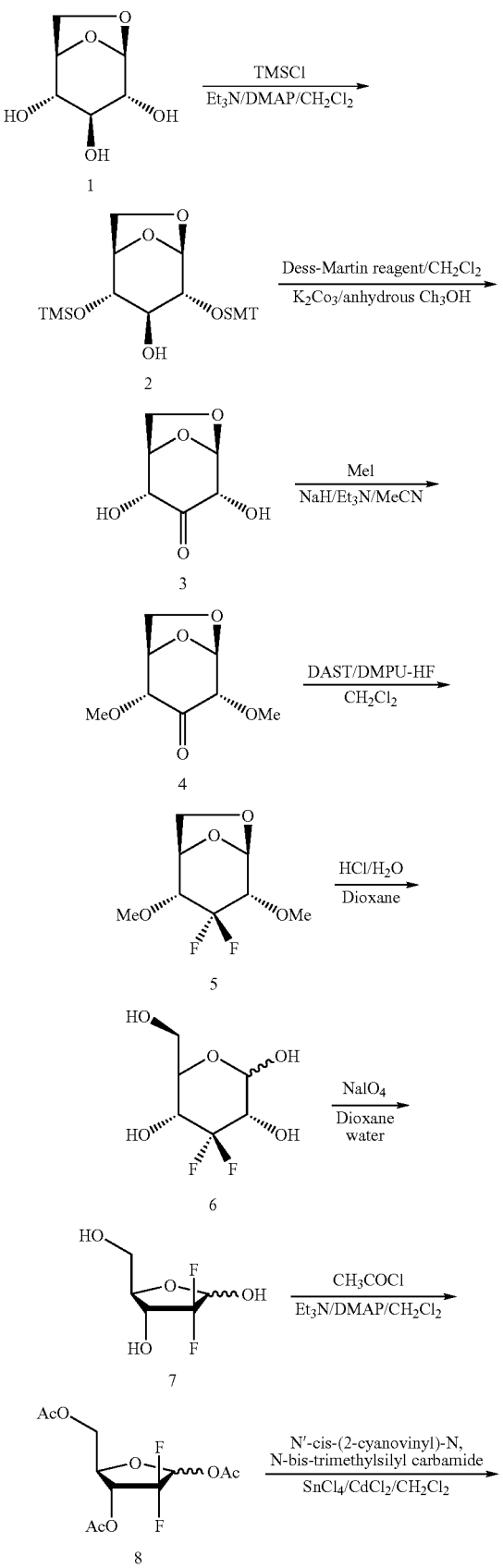

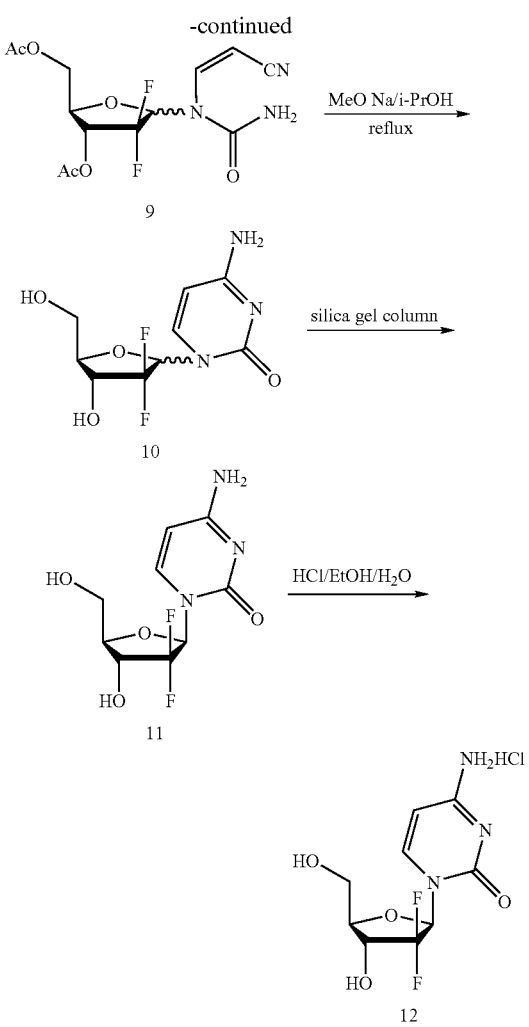

The process of synthesizing β-1-(2'-deoxy-2',2'-difluoro-D-ribofuranosyl)-4-amino-pyrimidine-2-one hydrochloride and its key intermediate 2-deoxy-2,2-difluoro-D-ribofuranose starting from 1,6-anhydro-β-D-glucose as the raw material is carried out in several steps. There are 9–10 intermediates produced in the process. In the synthetic Scheme provided by the present invention, some steps can proceed to next step only upon simple treatment. It can improve repeatability and be beneficial to large-scale production.

2,4-di-trimethylsiloxyl-1,6-anhydro-β-D-glucose (Compound 2) can be obtained starting from 1,6-anhydro-β-D-glucose (Compound 1), followed by selective silanization of hydroxyl group at position 2,4 of the 1,6-anhydro-β-D-glucose. It is also possible to use other groups to protect hydroxyl group at position 2,4. For the protection of hydroxyl group, Theodora W. Greene made a detailed description in "Protective Groups in Organic Synthesis" (John Wiley & Sons, Inc. 1991). Beside the use of trimethylsilyl group as protective group, it is also possible to use the following groups: triethylsilyl, dimethyl-t-butylsilyl, benzoyl, tosyl, benzyl, and methyl. Among them, trimethylsilyl is the most preferable. This is due to the fact that in the method of the present invention, the degree of conversion of trimethylsilyl protective group is not only high, but also its deprotection is easier to be carried out. In addition, the steric hindrance of the trimethylsilyl protective group is relatively smaller and thus is beneficial to the oxidation at position 3 of β-D-glucose in the next step. Other protective groups do not have the advantage of both high conversion and smaller steric hindrance.

Regarding the Compound 2, Cerny, M. et al. proposed in 1961 to use anhydrous pyridine as the solvent. Although both the conversion and selectivity were high, the post-treatment was much more complex due to the difficulty in removing pyridine and the reduced pressure distillation (0.1 mm Hg) is necessary to obtain final product (*Collection Czech. Chem. Communs.* 1961, 26:2542). In the method of the present invention, anhydrous aprotic solvents such as dichloromethane, chloroform, carbon tetrachloride, 1,2-dichloroethane, 1,1-dichloroethane, 1,1,1-trichloroethane, 1,1,2-trichloroethane, ethyl acetate, propyl acetate, anisole, 1,2-methoxyethane, dimethyl ether, ether, n-butyl ether, isopropyl ether, dioxane, acetonitrile, tetrahydrofuran, nitromethane, nitroethane, nitropropane are used as solvents. Diethylamine, triethylamine, n-propyl amine, di-isopropyl amine, n-butyl amine, isobutyl amine, 1,8-diazabicyclo (5.4.0.)undecene-7 (DBU), 2,6-dichlorobenzonitrile (DBN), N,N-dimethylphenylene urea (DMPU) or hexamethyl phosphamide (HMPA) is used as acid-binding agent. 4,4-dimethylaminopyridine is used as catalyst and the amount of the catalyst used is 0.01–5 mole % based on the amount of 1,6-anhydro-β-D-glucose. The ratio in mole of 1,6-anhydro-β-D-glucose to trimethylchlorosilane is in the range of 1:2.0–3.2. The reaction temperature is in a range between −10° C. and 40° C. and the reaction time is in the range of 5 min–24 hr. Thus Compound 2 can be prepared by above process. Preferably, the ratio in mole of 1,6-anhydro-β-D-glucose to trimethylchlorosilane is in the range of 1:2.0–2.2, the reaction temperature is in a range between −5° C. and 25° C., the reaction time is in the range of 10 min–10 hr, the amount of the catalyst used is 0.1–1 mole % based on the amount of 1,6-anhydro-β-D-glucose, and anhydrous dichloromethane or chloroform is used as reaction medium.

3-Carbonyl-1,6-anhydro-β-D-glucose (Compound 3) can be obtained by oxidation of Compound 2 and deprotection of trimethylsilyl protective group. The hydroxyl group at position 3 of Compound 2 is oxidized to ketone. The oxidizing agent is one or more selected from the group consisted of $PtO_2$, Pt, $CrO_3$, $Na_2CrO_7$, PCC, PDC, $KMnO_4$, $NaBrO_3$, dimethyl sulfoxide (DMSC)/dicyclohexyl carbodiimide(DCC), DMSO/$SOCl_2$, DMSO/$(CF_3COO)_2O$, DMSO/TsCl (p-methyl benzene sulfochloride), $ClO_2$, Dess-Martin reagent and the like. Among them, PCC, PDC and Dess-Martin reagent are used in anhydrous dichloromethane due to mild condition and high conversion. In particular, Dess-Martin reagent has advantage of both mild condition, high conversion and simple post-treatment. Thus trimethylsilyl protective group can easily be deprotected in dichloromethane-methanol mixed solvent and under the action of potassium carbonate and $BuN^+F^-$ to give Compound 3.

2,4-dimethyl-3-carbonyl-1,6-anhydro-β-D-glucose is obtained by reaction between Compound 3 and iodomethane in anhydrous organic amine and acetonitrile solvent and under action of strong alkaline catalyst. Dichloromethane is used to extract 2,4-dimethyl-3-carbonyl-1,6-anhydro-β-D-glucose. After purification, Compound 5 can be obtained by direct fluorination.

3-Deoxy-3,3-difluoro-2,4-dimethyl-1,6-anhydro-β-D-glucose (Compound 5) can be prepared by fluorination of 2,4-dimethyl-3-carbonyl-1,6-anhydro-β-D-glucose with conventional DAST fluorinating agent in anhydrous dichloromethane solvent. However, the efficiency of the fluorination is not satisfactory. The efficiency of the fluorination by using DMPU-HF fluorinating agent is also not satisfactory. When complex of DAST and DMPU are used simultaneously, not only conversion of fluorination is raised but also the reaction time is greatly shortened indicating strong synergistic effect. Therefore, the present invention actually provides another kind of fluorination method. By using the method, Compound 5 can be obtained conveniently.

The hydroxyl protective group at position 2,4 of 3-deoxy-3,3-difluoro-2,4-dimethyl-1,6-anhydro-β-D-glucose (Compound 5) can be deprotected under acidic condition. In strong acid medium, 1,6-deoxy can be hydrolyzed to form hydroxyl group. Therefore by using appropriate inorganic acid or organic acid, it is able to obtain 3-deoxy-3,3-difluoro-D-glucose (Compound 6) conveniently. The appropriate inorganic acids are hydrochloric acid or sulfuric acid, and the organic acid is trifluoroacetic acid.

The ortho-hydroxyl group of 3-deoxy-3,3-difluoro-D-glucose (Compound 6) can easily be oxidized under the action of strong oxidant and then condensed and dehydrated to form ribofuranose. The oxidant used to oxidize and decompose ortho-hydroxyl group is sodium periodate or lead tetra-acetate. The latter can react only under anhydrous condition and would cause pollution and difficulty in post-treatment. Thus it is better to use sodium periodate to oxidize and decompose the ortho-hydroxyl group of 3-deoxy-3,3-difluoro-D-glucose (Compound 6) and convert it into 2-deoxy-2,2-difluoro-D-ribofuranose (Compound 7).

Compound 8 can react with bis-trimethylsilylcytosine to yield the final product. In this case, it is necessary to protect the hydroxyl group of 2-deoxy-2,2-difluoro-D-ribofuranose (Compound 7) at first. There are already many methods for protection of hydroxyl group reported in literature such as Stephen Hanessian: "Preparative Carbohydrate Chemistry" (Marcel Dekker, Inc. 1997) and Theodora W. Greene: "Protective Groups in Organic Synthesis" (John Wiley & Sons, Inc. 1991). Since the reactivity of hydroxyl group at position 1 of Compound 6 is higher than those at position 3 and 5, it is necessary to protect hydroxyl group at position 1 firstly by "one kettle method" and then protect those at position 3 and 5. Since the condensation reaction of ribose and base cytosine occurs at position 1 of ribose in the form of SN2 displacement reaction, the protective group at position 1 is easier to be removed. Such kind of protective groups include methyl, mesyl, tosyl, acetyl and the like. Mesyl group or acetyl group is generally used as the protective group. Thus the leaving tendency of group at position 1 is increased and the occurrence of displacement reaction with cytosine is easier while the protective group at position 3 and 5 should be stable in the successive reaction and should be relatively easy to be removed. The protective group for position 3 and 5 can be benzoyl group, acetyl group and the like. However since the steric hindrance of amino group at position 1 of bis-trimethylsilylcytosine is relatively great together with the effect of 2 fluorine element at position 2 of the ribofuranose, the conversion rate of β-1-(2'-deoxy-2',2'-difluoro-D-ribofuranosyl)-4-aminopyrimidine-2-one is reduced. The present invention proposes the following method: Straight chain aliphatic hydrocarbon N'-cis-(2-cyanovinyl)-N,N-bistrimethysilyl urea recondenses with Compound 8 to form Compound 9. After distilling off the solvent and separating the product, Compound 9 is condensed and cyclized in strong alkaline methanol solution to yield Compound 10. The yield of Compound 10 based on Compound 8 is up to 30%–60%. Compound 10 is then eluted at a silica gel column to obtain β type Compound 11, which is salified in ethyl alcohol solution to form salt. Thus, β-1-(2'-deoxy-2', 2'-difluoro-D-ribofuranosyl)-4-aminopyrimidine-2-one i.e. 2'-deoxy-2',2'-difluoro-β-cytidine or pharmaceutically acceptable salt thereof is obtained.

The following embodiments are described thoroughly in order to understand the present invention more clearly. However, the scope of the present invention will not be limited by these examples.

EXAMPLE 1

Synthesis of 2,4-di-trimethylsiloxanyl-1,6-anhydro-β-D-glucose (Compound 2)

81 g of (0.5 mol) Compound 1,100 ml anhydrous triethylamine and 2 g of N',N-dimethylamino pyridine were dissolved in 400 ml anhydrous dichloromethane. Temperature was lowered to −10° C. 120 g trichloromethyl silyl was added slowly to the solution and the temperature of the reacting mixed solution was controlled in the range between −10° C. and −5° C. After the dropping, the solution was stirred for 2–3 hr at −10° C.−−5° C. and then continued the stirring for 5–8 hr. The course of the reaction was monitored by TLC. After the complete conversion of all raw materials, the reacting solution was poured into 2000 ml of water and stirred for 15 min. The organic phase was separated. The aqueous phase was extracted with dichloromethane for 3 times and the organic phase was combined with the former one. The combined organic phase was washed successively with appropriate amount of 1N HCl, water and saturated brine and then dried with anhydrous magnesium sulfate. Active carbon was added to decolor the dried solution. Filtered to give 150 g of Compound 2 (determined by HPLC, yield: 98%). Solvent in the solution did not need to distill off and the solution can be used to carry out the next reaction. A small amount of the solution was concentrated at 200° C.–230° C. by vacuum distillation (0.1 mm Hg) and a slightly pale yellow liquid was obtained with boiling point at 280° C.–285° C., $[\alpha]^{20}_D$ −32 ° (c 1.44, $CHCl_3$), $^1H$ NMR (300 Hz, CDCl), hydrogen proton of methyl at 2 and 4 position of Si: 0.08 ppm (—$CH_3$ s peak), 1.9 ppm (—OH s peak), MS: 307 ($M^+$).

EXAMPLE 2

Synthesis of 3-carbonyl-1,6-anhydro-β-D-glucose (Compound 3)

Anhydrous dichloromethane solution containing 140 g of the above-mentioned Compound 2 (0.46 mol) under $N_2$ bubbling was slowly added to a solution of 300 g of Dess-Martin reagent in 2000 ml of dichloromethane stored in an ice bath. The velocity of dropping was controlled so as to maintain the temperature of the mixture below 0° C. After the dropping was finished, the temperature was kept at that temperature for 60 min and then the solution was stirred at room temperature for 14 hr. The above-mentioned reacting mixture was poured into 9000 ml of saturated $NaHCO_3$ solution containing 1100 g of $Na_2S_2O_3.5H_2O$, and the mixture was stirred for 30 min. The organic phase was separated, washed with saturated $NaHCO_3$ solution, water and saturated brine successively, and dried with anhydrous magnesium sulfate. It was then filtered and distilled to remove solvent and an oily substance was obtained which was dissolved in 800 ml of anhydrous methanol. To the said methanol solution, 20 g of potassium carbonate was added and the solution was stirred at room temperature. The course of the reaction was monitored by TLC. After the completion of reaction, the solution was concentrated to dryness and ether was then added to it. The ether solution was washed with dilute sulfuric acid, water and saturated $NaHCO_3$ solution and dried with anhydrous potassium carbonate. After filtration, 71 g of syrupy Compound 3 was obtained, which was then directly used to the next reaction. Following analytical data was obtained for Compound 3: $^1$H NMR (300 Hz, CDCl), 2.0 ppm (—OH s peak), MS: 161 (M$^+$).

EXAMPLE 3

Synthesis of 2,4-dimethyl-3-carbonyl-1,6-anhydro-β-D-glucose (Compound 4)

71 g of Compound 3 and 50 ml anhydrous triethylamine were dissolved in 500 ml anhydrous acetonitrile and 36 g of 60% NaH was added. After stirring for 60 min, solution of 130 g of methyl iodide and 150 ml anhydrous acetonitrile was added dropwise. The mixture was kept at 45–50° C. for 5–6 hr. TLC was used to monitor the reaction. After the completion of reaction, the temperature was lowered and 1000 ml of dichloromethane was added. The solution was washed with 5% $NaHCO_3$ solution, water and saturated brine successively, and dried with anhydrous potassium carbonate. It was then filtered and an anhydrous dichloromethane solution containing 80 g Compound 4 was obtained which was then directly used to the next reaction. Following analytical data was obtained for Compound 4: $^1$H NMR (300 Hz, CDCl), 3.3 ppm (—CH$_3$ s peak), MS: 189 (M$^+$).

EXAMPLE 4

Synthesis of 3-deoxy-3,3-difluoro-2,4-dimethyl-1,6-anhydro-β-D-glucose (Compound 5)

The above-mentioned solution containing 80 g (0.43 mol) Compound 4 and 500 ml anhydrous dichloromethane was stirred at room temperature with $N_2$ bubbling and 280 ml (2.13 mol) DAST and 3 ml DMPU-20HF were added. Stirring at room temperature was continued for 30–60 min. In the ice bath, saturated $NaHCO_3$ solution was slowly added. The organic phase was washed with water and saturated brine until neutral. Dichloromethane was distilled off and 82 g of Compound 5 was obtained, which was used directly in the next reaction without purification. A little amount of residue was purified by elution at silica gel column to obtain Compound 5. Following analytical data was obtained for Compound 5: $^1$H NMR (300 Hz, CDCl), 3.3 ppm (—CH$_3$ s peak), MS: 211 (M$^+$).

EXAMPLE 5

Synthesis of 2'-deoxy-2',2'-difluoro-D-ribofuranose (Compound 7)

82 g (0.39 mol) of Compound 5 obtained in the above reaction was dissolved in 600 ml of dioxane and 4M, 200 ml HCl and 4 g of active carbon was added. The mixture was bubbled with $N_2$, refluxed with heating for 5–8 hr. The reaction was monitored by TLC. After completion of degradation, the mixture was cooled to 40° C.–50° C. and 4 g of active carbon was added and stirred until room temperature. After filtration, 1000 ml of dioxane and 400 ml of water were added. The pH of the reacting mixture was adjusted to 5–6 by 4N KOH solution and then 520 g of sodium periodate was added with stirring. The solution was bubbled with $N_2$ and stirred at 30–400° C. for 10 hr, refluxed for 5–6 hr, distill off the solvent, diluted with dichloromethane, filtered off the solid, eluted with dichloromethane, the organic phase was combined, dried with anhydrous sodium sulfate to obtain 45 g of syrupy Compound 7. A little amount of Compound 7 was purified with TLC and α/β-(Compound 7). α-Compound 7: $^1$H NMR (300 Hz, CDCl), 5.50 ppm (m, 1H, $_{H1}$), 5.53 ppm (m, 1H, $_{H3}$), 4.79 ppm (m, 1H, $_{H4}$), 4.70–4.61 ppm (m, 2H, $_{H5}$); β-(Compound 7): 5.76 ppm (m, 1H, $_{H1}$), 5.41 ppm (m, 1H, $_{H3}$), 4.47 ppm (m, 1H, $_{H4}$), 4.65 ppm (m, 2H, $_{H5}$), MS: 171 (M$^+$), content of fluorine, calcd. for: 22.34%, found: 22.29%.

EXAMPLE 6

Synthesis of 2-deoxy-2,2-difluoro-1,3,5-triacetyl-D-ribofuranose (Compound 8)

45 g (about 0.265 mol) Compound 7 slurry was dissolved in 300 ml anhydride dichloromethane. 150 ml of triethyl amine and 5 g DMAP was added. At room temperature, a solution of 70 g acetyl chloride and 200 ml anhydrous dichloromethane was slowly added and the mixture was stirred at room temperature overnight. The solution was washed with saturated $NaHCO_3$ solution, water and saturated brine until neutral. Anhydrous sodium sulfate was used to dry the solution. After filtration, anhydrous dichloromethane solution of 75 g syrupy Compound 8 was obtained which can be used in the next reaction directly.

EXAMPLE 7

Synthesis of α/β-1-(2'-deoxy-2',2'-difluoro-D-ribofuranosyl)-4-aminopyrimidine-2-one (Compound 10)

83 g of cis-2-cyanovinyl urea was dissolved in 200 ml hexamethyldisilazane and 5 ml of trimethylchlorosilane and 1 g of lithium chloride were added. $N_2$ was bubbled and the solution was refluxed until clear. Hexamethyldisilazane was then distilled off and N,N-bistrimethylsilyl-(cis-2-cyanovinylurea) was obtained, which was then dissolved in 200 ml anhydrous dichloromethane. To the solution, 1 g of $CdCl_2$ was added and the solution was stirred with $N_2$ bubbling.

To the anhydrous dichloromethane solution of Compound 8 obtained in Example 6, more anhydrous dichloromethane was added until the total volume up to 700 ml. The temperature of the solution was lowered to 0° C. Mixed solution of 100 ml anhydrous $SnCl_4$ and 100 ml anhydrous dichloromethane was added dropwisely and the temperature of the solution was kept below 5° C. After stirring for 20 hr, $CdCl_2$-anhydrous dichloromethane solution of N,N-bistrisilyl-(cis-2-cyanovinylurea) prepared above was added. The solution was stirred for 2–3 hr at room temperature and refluxed overnight. After cooling, 800 ml saturated $NaHCO_3$ solution was poured therein. Insoluble material was filtered off and the organic phase was dried with anhydrous magnesium sulfate. After filtration and distilling off the solvent, the residue was dissolved in 500 ml isopropyl alcohol and 18 g of sodium ethoxide was added. After the solution was stirred homogeneously, it was heated and refluxed for 1–6 hr. The solvent in the refluxed solution was vacuum-distilled off and the residue was dissolved in 500 ml dichloromethane, washed with $H_2O$, 1N HCl and saturated NaCl solution and dried by anhydrous magnesium sulfate. After being concentrated and being eluted with chloroform/methanol as the eluent at silica gel column of 5 cm×25 cm, 8.4 g of crystalline Compound 11 of β-1-(2'-deoxy-2',2'-difluoro-D-ribofuranosyl)-4-aminopyrimidine-2-one was obtained. The data of the optical rotation and various spectrometry of the obtained Compound 11 were identical with those reported by Chou, T. S. in Synthesis, 1992, 565. i.e. $[\alpha]_D$ (c=0.98, MeOH) +69.85°; $[\alpha]_{365}$ +410.40°, elemental analysis: $C_9H_{11}F_2N_3O_4$: calcd. for: C, 41.07; H, 4.21; F, 14.44; N, 15.97; found C, 41.11; H, 4.28; F, 14.50; N, 15.60; IR (KBr): υ=3486, 3340, 1656, 1621, 1033 cm$^{-1}$, $^{13}$C NMR(D$_2$O) δ=59.86 (C-5') 69.20 (C-3'), 80.70 (C-4'), 84.50 (C-1'), 95.24 (C-5), 123.63 (C-2'), 141.83 (C-6), 153.81 (C-2), 166.20 (C-4).

EXAMPLE 8

Synthesis of β-1-(2'-deoxy-2,'2'-difluoro-D-ribofuranosyl)-4-aminopyrimidine-2-one hydrochloride
(Compound 12)

8.4 g of Compound 11 i.e. β-1-(2'-deoxy-2'2'-difluoro-D-ribofuranosyl)-4-aminopyrimidine-2-one was mixed with 20 ml deionized water. At 0° C., 4N HCl was slowly dropped into the mixture until complete dissolution of Compound 11. Then 50–100 times of volume of anhydrous ethanol was added and the temperature of the solution was lowered to −5° C. While maintaining at this temperature, the solution was stirred, filtered and washed with cool anhydrous ethanol and then dried in vacuum. Finally 6.2 g of Compound 12 was obtained. The data of the optical rotation and various spectrometry of the obtained Compound 12 were identical with those reported by Chou, T. S. in Synthesis, 1992, 565. i.e. $[\alpha]_D$ (c=1.0, D$_2$O) +47.56°; $[\alpha]_{365}$ +255.7°, elemental analysis: $C_9H_{11}ClF_2N_3O_4$: calcd. for: C, 36.07; H, 4.04; Cl, 11.83; F, 12.68; N, 14.02. found: C, 36.13; H, 4.10; Cl, 11.90; F, 12.63; N, 13.89. IR (KBr): υ=3490, 3345, 1660, 1623, 1036 cm$^{-1}$, $^{13}$C NMR (D$_2$O) δ=61.01 (C-5'), 70.12 (C-3'), 82.16 (C-4'), 85.50 (C-1'), 97.40 (C-5), 124.03 (C-2'), 145.16 (C-6), 150.56 (C-2), 164.23 (C-4).

What is claimed is:

1. A method for preparing 2'-deoxy-2',2'-difluoro-β-cytidine or pharmaceutically acceptable salts thereof via 2-deoxy-2,2-difluoro-D-ribofuranose as intermediate, comprising obtaining 1,6-anhydro-β-D-glucose as raw material, oxidizing, and fluorinating to obtain 2-deoxy-2,2-difluoro-D-ribofuranose as intermediate.

2. The method according to claim 1, further comprising:
    (1) oxidizing 1,6-anhydro-β-D-glucose to give 3-carbonyl-1,6-anhydro-β-D-glucose;
    (2) fluorinating and hydrolyzing 3-carbonyl-1,6-anhydro-β-D-glucose to obtain 3-deoxy-3,3-difluoro D-glucose;
    (3) condensing and dehydrating 3-deoxy-3,3-difluoro-D-glucose to obtain 2-deoxy-2,2-difluoro-ribofuranose; and
    (4) preparing 2'-deoxy-2',2'-difluoro-β-cytidine or pharmaceutically acceptable salt thereof from 2-deoxy-2,2-difluoro-D-ribofuranose.

3. The method according to claim 2, wherein in step (1), steps of protection and deprotection of hydroxyl groups of 1,6-anhydro-β-D glucose at position 2 and 4 are included.

4. The method according to claim 3, wherein the protecting group for hydroxyl group is trimethylsilyl group.

5. The method according to claims 3 or 4, wherein in step (1), the protection of hydroxyl group is carried out in one or more anhydrous aprotic solvents selected from the group consisting of: dichloromethane, chloroform, carbon tetrachloride, 1,2-dichloroethane, 1,1-dichloroethane, 1,1,1-trichloroethane, 1,1,2-trichloroethane, ethyl acetate, propyl acetate, anisole, 1,2-methoxyethane, diethylene glycol ether, ethyl ether, n-butyl ether, isopropyl ether, dioxane, acetonitrile, tetrahydrofuran, nitromethane, nitroethane, and nitropropane.

6. The method according to claim 5, wherein the anhydrous aprotic solvents are anhydrous dichloromethane or chloroform.

7. The method according to claims 3 or 4, wherein in step (1), the protection of hydroxyl group is carried out by using one or more acid-binding agents selected from the group consisting of: diethylamine, triethylamine, n-propyl amine, di-isopropyl amine, n-butyl amine, isobutyl amine, 1,8-diazabicyclo(5.4.0)undecene-7 (DBU),2,6-dichlorobenzonitrile (DBN),N,N-dimethylphenylene urea (DMPU) and hexamethylphosphamide (HMPA).

8. The method according to claims 3 or 4, wherein in step (1), the protection of hydroxyl group is carried out by using 4,4-dimethylaminopyridine as the catalyst and the amount of the catalyst used is 0.01–5 mole % based on the amount of 1,6-anhydro-β-D-glucose.

9. The method according to claim 8, wherein the amount of the catalyst is 0.1–1 mole % based on the amount of 1,6-anhydro-β-D-glucose.

10. The method according to claims 3 or 4, wherein in the protection of hydroxyl group of step (1), the used ratio in mole of 1,6-anhydro-β-D-glucose to trimethylchlorosilane is 1:2.0–3.2, the reaction temperature is in a range between −10° C. and 40° C., and the reaction time is in the range of 5 min–24 hr.

11. The method according to claim 10, wherein in the protection of hydroxyl group of step (1), the used ratio in mole of 1,6-anhydro-β-D-glucose to trimethylchlorosilane is 1:2.0–2.2, the reaction temperature is in a range between −5° C. and 25° C., and the reaction time is in the range of 10 min–10 hr.

12. The method according to claim 2, wherein in step (1), the oxidant used in the oxidation is one or more selected from the group consisted of: $PtO_2$, Pt, $CrO_3$, $Na_2CrO_7$, pyridinium chlorochromate (PCC),1,2-dichloropropylene (PDC), $KMnO_4$, $NaBrO_3$, dimethyl sulfoxide(DMSO)/dicyclohexyl carbodiimide(DCC), DMSO/SOCl$_2$, DMSO/(CF$_3$COO)$_2$O, DMSO/p-methyl benzene sulfochloride (TsCl), ClO$_2$, and Dess-Martin reagent.

13. The method according to claim 12, wherein the oxidant is PCC, PDC or Dess-Martin reagent.

14. The method according to claim 13, wherein the oxidant is Dess-Martin reagent.

15. The method according to claim 2, wherein in step (2), steps of protection and deprotection of hydroxyl groups of 3-carbonyl-1,6-anhydro-β-D glucose at position 2 and 4 are included.

16. The method according to claim 15, wherein in step (2), the deprotection is carried out in the presence of one or more strong acids selected from the group consisting of: hydrochloric acid, sulfuric acid and trifluoroacetic acid.

17. The method according to claim 2, wherein in the fluorination of step (2), the fluorinating agent is a complex of diethylamino sulfur trifluoride and N,N-dimethylpropylene urea-hydrogen fluoride.

18. The method according to claim 2, wherein in step (3), the ortho-hydroxyl group of 3-deoxy-3,3-difluoro-D-glucose is oxidized by sodium periodate, condensed and dehydrated to obtain 2-deoxy-2 2-difluoro-D-ribofuranose.

19. The method according to claim 2, wherein in step (4), steps of protection and deprotection of hydroxyl group of 2-anhydro-2 2-difluoro-D-ribofuranose are included.

20. The method according to claim 19, wherein the hydroxyl group at position 1 is protected first and then those at positions 3 and 5 are protected, wherein the protective group for protecting hydroxyl group at position 1 is mesyl group or acetyl group and those at positions 3 and 5 are benzoyl group or acetyl group.

21. The method according to claim 2, wherein in step (4), 2,2-deoxy-2,2-difluoro-D-ribofuranose is condensed with N'-cis-(2-cyanovinyl)-N,N-bis-trimethylsilyl urea, condensed and cyclized in methanol under the action of strong alkali, purified and salified to obtain 2'-deoxy-2',2'-difluoro-β-cytidine or pharmaceutically acceptable salt thereof.

22. The method according to claim 1 or 2, wherein the pharmaceutically acceptable salt of 2'-deoxy-2',2'-difluoro-β-cytidine is 2'-deoxy-2',2'-difluoro-β-cytidine hydrochloride.

* * * * *

UNITED STATES PATENT AND TRADEMARK OFFICE
CERTIFICATE OF CORRECTION

PATENT NO. : 7,214,791 B2
APPLICATION NO. : 10/883462
DATED : May 8, 2007
INVENTOR(S) : Chen Gong It is certified that error appears in the above-identified patent and that said Letters Patent is hereby corrected as shown below:

At column 2, line 29-30, please delete "β-D glucose" and insert -- β-D-glucose --, therefor.

At column 2, line 45, please delete "(5.4.0.)undecene-7" and insert -- (5.4.0.) undecene-7 --, therefor.

(Consider Space)

At column 3, line 17 (Approx.), please delete "-2 2" and insert -- -2,2 --, therefor.

At column 6, line 44, please delete "of" and insert -- of: --, therefor.

At column 7, line 60, please delete "bistrimethysilyl" and insert -- bistrimethylsilyl --, therefor.

At column 10, line 1, please delete "400°C." and insert -- 40°C. --, therefor.

At column 11, line 8, please delete "found" and insert -- found: --, therefor.

At column 11, line 8, please delete "15.60;" and insert -- 15.60. --, therefor.

At column 11, line 10, please delete "(C-5')" and insert -- (C-5'), --, therefor.

At column 11, line 16, please delete "-2,'2'" and insert -- -2',2' --, therefor.

At column 11, line 20, please delete "-2'2'" and insert -- -2',2' --, therefor.

At column 11, line 34, please delete "14.02." and insert -- 14.02; --, therefor.

At column 11, line 50, Claim 2, please delete "difluoro D-glucose;" and insert -- difluoro-D-glucose; --, therefor.

At column 12, line 50 (Approx.), Claim 15, please delete "β-D glucose" and insert -- β-D-glucose --, therefor.

At column 12, line 64, Claim 18, please delete "-2 2" and insert -- -2,2 --, therefor.

UNITED STATES PATENT AND TRADEMARK OFFICE
CERTIFICATE OF CORRECTION

PATENT NO. : 7,214,791 B2
APPLICATION NO. : 10/883462
DATED : May 8, 2007
INVENTOR(S) : Chen Gong It is certified that error appears in the above-identified patent and that said Letters Patent is hereby corrected as shown below:

At column 12, line 67, Claim 19, please delete "-2 2" and insert -- -2,2 --, therefor.

Signed and Sealed this

Twenty-seventh Day of November, 2007

JON W. DUDAS
*Director of the United States Patent and Trademark Office*